(12) United States Patent
Levinski (10) Patent No.: US 10,337,991 B2
(45) Date of Patent: Jul. 2, 2019

(54) CONTROL OF AMPLITUDE AND PHASE OF DIFFRACTION ORDERS USING POLARIZING TARGETS AND POLARIZED ILLUMINATION

(71) Applicant: KLA-Tencor Corporation, Milpitas, CA (US)

(72) Inventor: Vladimir Levinski, Migdal HaEmek (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/115,752

(22) PCT Filed: Jun. 1, 2016

(86) PCT No.: PCT/US2016/035190
§ 371 (c)(1),
(2) Date: Aug. 1, 2016

(87) PCT Pub. No.: WO2017/099843
PCT Pub. Date: Jun. 15, 2017

(65) Prior Publication Data
US 2018/0031470 A1    Feb. 1, 2018

Related U.S. Application Data

(60) Provisional application No. 62/264,514, filed on Dec. 8, 2015.

(51) Int. Cl.
*G01N 21/47* (2006.01)
*G01B 11/25* (2006.01)
(Continued)

(52) U.S. Cl.
CPC ............. *G01N 21/47* (2013.01); *G01B 11/24* (2013.01); *G01B 11/2513* (2013.01);
(Continued)

(58) Field of Classification Search
CPC ........... G01N 21/47; G01N 2021/4792; G01B 11/2536; G01B 11/2513; G03F 7/70633
See application file for complete search history.

(56) References Cited

U.S. PATENT DOCUMENTS 5,274,420 A * 12/1993 Chastang ............... G02B 3/005
250/492.2
5,486,923 A    1/1996 Mitchell et al.
(Continued)

FOREIGN PATENT DOCUMENTS

WO    9622506    7/1996
WO    2016086056 A1    6/2016

OTHER PUBLICATIONS

ISA/KR, International Search Report for PCT/US2016/035190 dated Aug. 19, 2016.

*Primary Examiner* — Dominic J Bologna
(74) *Attorney, Agent, or Firm* — Hodgson Russ LLP (57) ABSTRACT

Metrology scatterometry targets, optical systems and corresponding metrology tools and measurement methods are provided. Targets and/or optical systems are designed to enhance first order diffraction signals with respect to a zeroth order diffraction signal from the scatterometry target by creating a phase shift of 180° between zeroth order diffraction signals upon illumination of the scatterometry targets. For example, the targets may be designed to respond to polarized illumination by producing a first phase shift between zeroth order diffraction signals upon illumination thereof and optical systems may be designed to illuminate the target by polarized illumination and to analyze a resulting diffraction signal to yield a second phase shift between zeroth order diffraction signals upon illumination thereof. The phase shifts add up to 180° to cancel out the zeroth order diffraction signals, with either phase shift being between 0 and 180°.

23 Claims, 9 Drawing Sheets

(51) Int. Cl.
*G01B 11/24* (2006.01)
*G01N 21/00* (2006.01)
*G03F 7/20* (2006.01)

(52) U.S. Cl.
CPC ......... *G01B 11/2536* (2013.01); *G01N 21/00* (2013.01); *G03F 7/70683* (2013.01); *G01B 2210/56* (2013.01); *G01N 21/4788* (2013.01); *G01N 2021/4792* (2013.01); *G03F 7/70633* (2013.01)

(56) References Cited

U.S. PATENT DOCUMENTS

| | | | | |
|---|---|---|---|---|
| 5,715,039 | A * | 2/1998 | Fukuda | G03F 7/70125 355/53 |
| 6,992,764 | B1 * | 1/2006 | Yang | B23K 26/04 356/369 |
| 7,608,468 | B1 * | 10/2009 | Ghinovker | G03F 7/70633 356/401 |
| 2002/0015900 | A1 * | 2/2002 | Petersen | G03F 1/29 430/5 |
| 2005/0088744 | A1 * | 4/2005 | Smith | G02B 5/1861 359/566 |
| 2009/0059375 | A1 | 3/2009 | Hoose | |
| 2010/0328655 | A1 * | 12/2010 | Den Boef | G03F 7/70633 356/237.5 |
| 2016/0313658 | A1 | 10/2016 | Marciano et al. | |
| 2017/0146915 | A1 | 5/2017 | Levinski et al. | |

\* cited by examiner

201 — ENHANCING FIRST ORDER DIFFRACTION SIGNALS WITH RESPECT TO A ZEROTH ORDER DIFFRACTION SIGNAL FROM A SCATTEROMETRY TARGET HAVING A COARSE PITCH, BY DESIGNING THE SCATTEROMETRY TARGET AND/OR BY CONFIGURING A METROLOGY TOOL'S OPTICAL SYSTEM TO YIELD A PHASE SHIFT OF 180° BETWEEN ZEROTH ORDER DIFFRACTION SIGNALS UPON ILLUMINATION OF THE SCATTEROMETRY TARGET

202 — COMBINING A FIRST PHASE SHIFT BY TARGET DESIGN WITH A SECOND PHASE SHIFT BY OPTICAL SYSTEM CONFIGURATION, THE FIRST AND SECOND PHASE SHIFTS ADD UP TO 180°

205 — DESIGNING POLARIZATION-SENSITIVE SCATTEROMETRY TARGETS WHICH ENHANCE FIRST ORDER DIFFRACTION SIGNALS BY THEIR RESPONSE TO POLARIZED ILLUMINATION

210 — COMBINING POLARIZATION CONTROL HARDWARE AND POLARIZING TARGETS TO PROVIDE ADDITIONAL DIFFRACTION ORDERS' PARAMETERS

220 — SEGMENTING TARGET ELEMENTS OF THE TARGET'S PERIODIC STRUCTURE(S) WITH FINE PITCH(ES) WHICH ARE NOT RESOLVED BY THE METROLOGY TOOL, ALONG TWO OR MORE DIRECTIONS

CONTROL OF AMPLITUDE AND PHASE OF DIFFRACTION ORDERS USING POLARIZING TARGETS AND POLARIZED ILLUMINATION

CROSS REFERENCE TO RELATED APPLICATIONS

This application claims the benefit of U.S. Provisional Patent Application No. 62/264,514 filed on Dec. 8, 2015, which is incorporated herein by reference in its entirety.

BACKGROUND OF THE INVENTION

1. Technical Field

The present invention relates to the field of metrology, and more particularly, to polarizing targets and corresponding polarization control in the optical system of the metrology tool.

2. Discussion of Related Art

Current methods for optical overlay measurement rely on two main technologies: imaging and Scatterometry. In imaging, the position of periodic targets is measured in the field of view of the optical system and the overlay (OVL) is deduced from positions of targets printed in different layers. Scatterometry utilizes interference between electromagnetic (EM) waves scattered by periodic overlay marks (targets with periodic structures) printed at different layers to deduce the relative displacement of the layers. In both cases a control on amplitudes and phases of the diffraction orders of the scattered EM waves may provide a crucial effect on accuracy and precision of overlay measurement.

SUMMARY OF THE INVENTION

The following is a simplified summary providing an initial understanding of the invention. The summary does not necessarily identify key elements nor limits the scope of the invention, but merely serves as an introduction to the following description.

One aspect of the present invention provides a method comprising enhancing first order diffraction signals with respect to a zeroth order diffraction signal from a scatterometry target having a coarse pitch, by designing the scatterometry target and/or by configuring a metrology tool's optical system to yield a phase shift of 180° between zeroth order diffraction signals upon illumination of the scatterometry target.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

The inventors have found out that, when target asymmetry is present, the mechanism of target asymmetry amplification is connected to the value of the difference in topographic phases between the first diffraction orders in the case of scatterometry OVL (+1 and −1, from upper and bottom gratings); and that the mechanism of target asymmetry amplification is connected to the value of the difference in the topographic phases between first and zero diffraction orders in the case of imaging OVL (±1 and 0, from upper and bottom gratings). Any hardware (HW) possibility for topographic phase control may significantly improve the accuracy of OVL measurement.

The inventors have additionally found out that another relatively common measurement problem occurs when there is a large difference between amplitudes of zero and other diffraction orders which causes a very low image contrast. The same problem appears in scatterometry OVL when amplitudes of first diffraction orders from two measured layers differ by more than an order of magnitude. In these cases the reduction of amplitude of the appropriate diffraction order may significantly improve both precision and accuracy of the measurement.

The following related documents, which are incorporated herein by reference in their entirety, may be integrated with the present disclosure to achieve mutual enhancement of accuracy, and such combinations are considered to be part of the present invention: (i) WIPO Patent Publication No. PCT/US15/62523 discloses deriving a partially continuous dependency of metrology metric(s) on recipe parameter(s), analyzing the derived dependency, determining a metrology recipe according to the analysis, and conducting metrology measurement(s) according to the determined recipe. (ii) Patent Application No. 62/222724 discloses different approaches (mostly HW options) for topographic phase control and provides a practical criterion for choosing the most appropriate recipe setup. (iii) An internal document discloses controlling the amplitude and phase of the zero diffraction order for improved precision and accuracy of overlay measurement. For example, the document discloses the implementation of HW options for zero diffraction order control, including leaky blocker, usage of adaptive optical element and interferential control. The present disclosure focuses on using polarizing targets and polarization control HW to provide an additional control level over the diffraction orders parameters. Moreover, the present disclosure uses relatively simple HW, is associated with the target design procedures and, while exemplified in a non-limiting manner to first diffraction order signals, is applicable to any diffraction order.

Metrology scatterometry targets, optical systems and corresponding metrology tools and measurement methods are provided. Targets and/or optical systems are designed to enhance first order diffraction signals with respect to a zeroth order diffraction signal from the scatterometry target by creating a phase shift of 180° between zeroth order diffraction signals upon illumination of the scatterometry targets. For example, the targets may be designed to respond to polarized illumination by producing a first phase shift between zeroth order diffraction signals upon illumination thereof and optical systems may be designed to illuminate the target by polarized illumination and to analyze a resulting diffraction signal to yield a second phase shift between zeroth order diffraction signals upon illumination thereof. The phase shifts add up to 180° to cancel out the zeroth order diffraction signals, with either phase shift being between 0 and 180°.

Figure 1A:
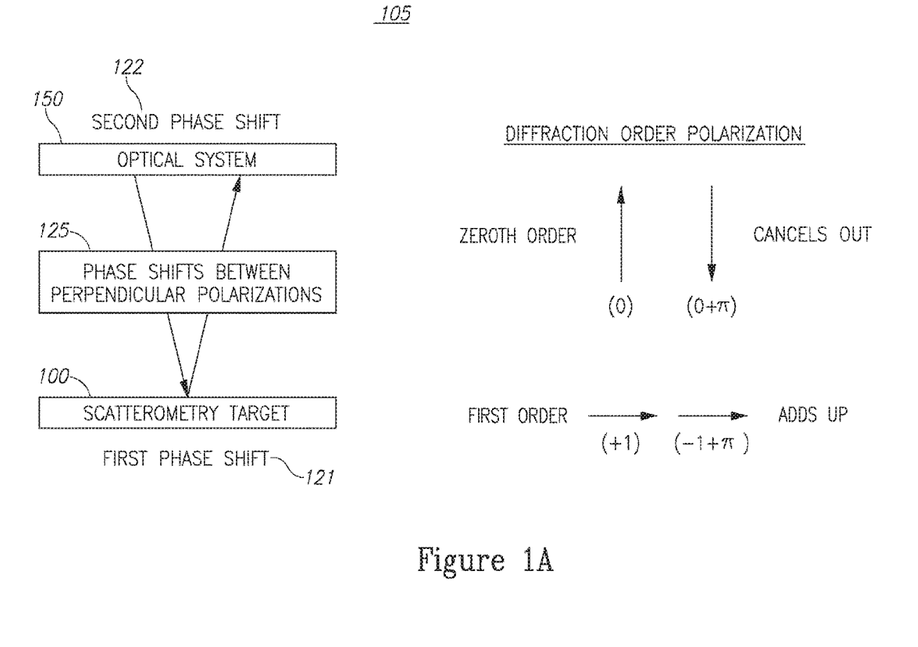
FIG. 1A is a high level schematic illustration of a metrology system implementing polarization phase control to cancel out zeroth order diffraction signals, according to some embodiments of the invention.

FIG. 1A is a high level schematic illustration of a metrology system 105 implementing polarization phase control to cancel out zeroth order diffraction signals, according to some embodiments of the invention. Metrology system 105 comprises a scatterometry metrology target 100 and a metrology tool having an optical system 150. Scatterometry metrology target 100 has a coarse pitch and is configured to yield a first phase shift 121 between zeroth order diffraction signals upon illumination thereof. Optical system 150 is configured to illuminate target 100 by two perpendicularly-polarized illumination components and to analyze a resulting diffraction signal at two perpendicular polarization directions that complement the two perpendicularly-polarized illumination components to yield a second phase shift 122 between zeroth order diffraction signals upon illumination thereof. The sum of first phase shift 121 and second phase shift 122 is 180° to cancel out the zeroth order diffraction signals. FIG. 1A illustrates schematically the diffraction orders' polarization—zeroth order components are canceled out by the addition of the 180° phase while first diffraction orders are enhanced by the addition of the −1 order with the added 180° phase to the +1 order. Metrology system 105 may be configured to cancel out the zeroth order diffraction signals by means of target design alone, by means of optical system design alone, or by means of combined adjustments to the target design and to the optical system design, as explained below.

Figure 1B:
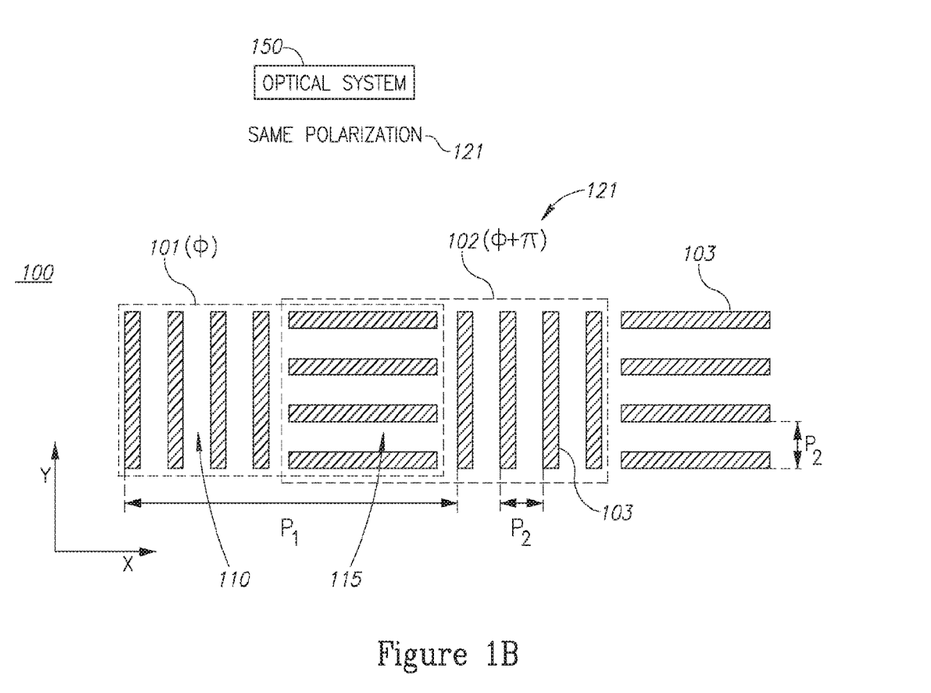
FIGS. 1B, 1C, 2A and 2B are high level schematic illustrations of scatterometry targets, according to some embodiments of the invention.

FIG. 1B is a high level schematic illustration of scatterometry target 100, according to some embodiments of the invention. Target 100 is configured to change the polarization of the diffraction signals with respect to the illumination, and is hence referred to as a polarizing target. Target 100 may be measured to provide diffraction signals in association with an optical system configured to provide and robust hardware polarization control (see system 150 below as an exemplary non-limiting option). Target 100 has a coarse pitch $P_1$ which is well-resolved by the metrology tool (e.g., 1000-2000 nm). Target 100 is configured to yield a phase shift of 180° between zeroth order diffraction signals upon illumination thereof, e.g., by having perpendicularly polarizing elements 103 at half the coarse pitch to yield the 180° phase shift. A part 110 of the coarse pitch area, e.g., a half thereof, is segmented in one direction (e.g., X) by a finer, unresolved pitch $P_2$ while another part 115, e.g., the other half of the coarse pitch area, is segmented by same fine segmentation pitch $P_2$ in a perpendicular direction to the first direction (e.g., Y). As a result, first diffraction order signals from polarized illumination in the X and Y directions have a phase difference of 180° ($\pi$) because target unit cells 101, 102 are shifted by half the pitch ($P_1$). Therefore, zeroth order signals from cells 101 and 102 cancel each other out while first order signals from cells 101 and 102 add up due to the inherent phase of 180° ($\pi$) between the +1 and −1 diffraction order signals. For pitches larger than 2λ, second and higher diffraction orders may be included, and the phase difference may be used to remove/enhance them as well (e.g., 180° phase difference removes even diffraction orders and enhances odd diffraction orders).

Figure 1C:
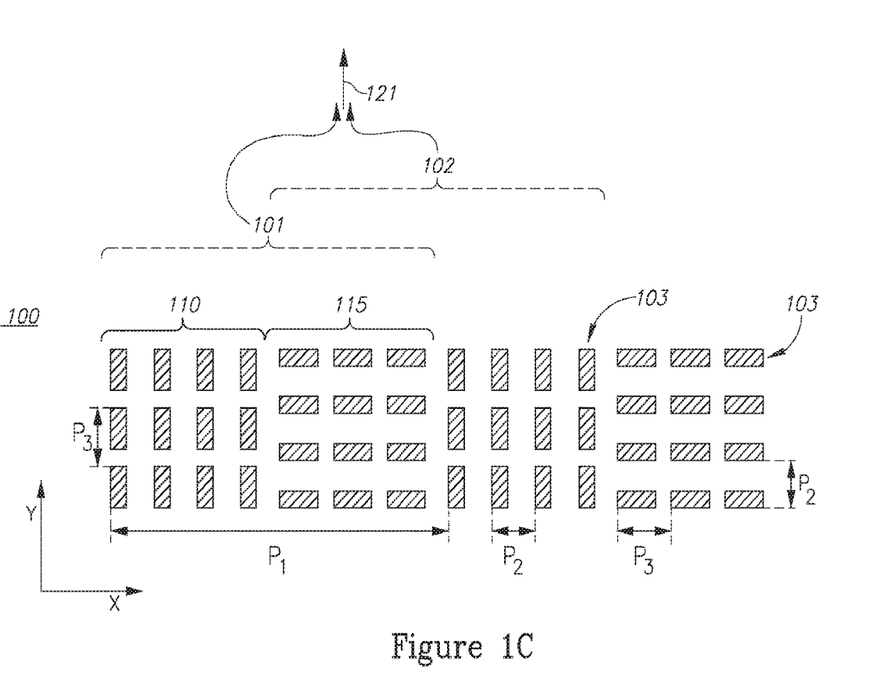

FIG. 1C is a high level schematic illustration of scatterometry target 100, according to some embodiments of the invention. Target 100 may be segmented in both directions to enhance its process compatibility. Perpendicularly polarizing elements 103 may be segmented with a fine pitch. In FIG. 1C, an additional segmentation with pitch $P_3$ is added to the target design illustrated in FIG. 1B. Both fine pitch segmentations may be performed with the same pitches in the X and Y directions, in order to avoid second order polarization effects and breaking of the symmetry between target sub cells 101, 102.

Targets 100 may be configured, by selecting target pitches (e.g., any of $P_1$, $P_2$, $P_3$), field fill factor (duty cycle), segmentation type etc. In the case of side by side imaging targets, additional features may be configured to optimize the target design, e.g., using unresolved periodic structures in one layer for measurement of periodic structures in another layer (e.g., using unresolved periodic structures in the upper layer for bottom grating measurements and vice versa).

Figure 2A:
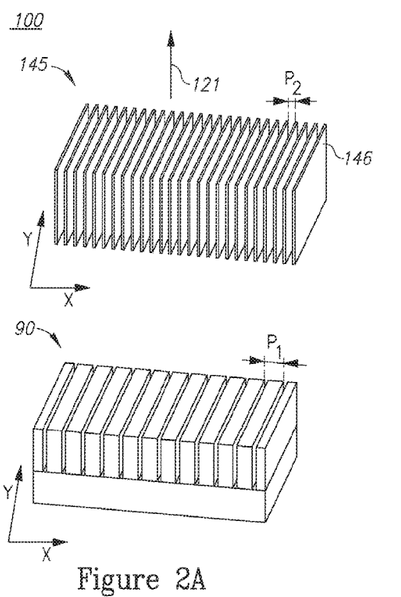
Figure 2B:
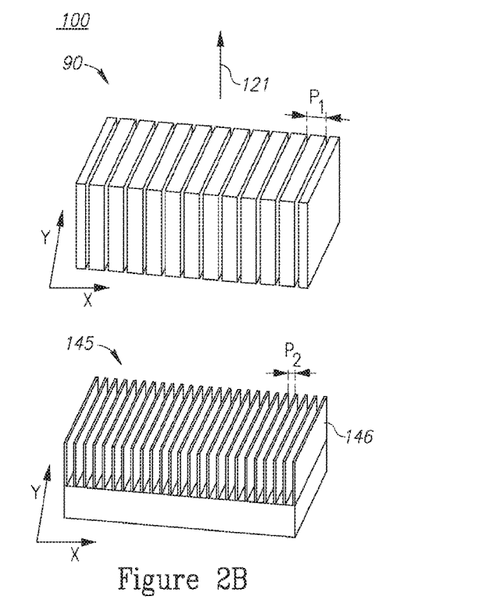

FIGS. 2A and 2B are high level schematic illustrations of scatterometry targets 100, according to some embodiments of the invention. Targets 100 comprise initial non-polarizing structures 90 (having a resolved pitch $P_1$), and at least one additional target layer 145 having at least one polarizing structure 146 (having a finer, non-resolved pitch $P_2<P_1$, also termed dummy structures) that is configured to yield the phase shift of 180° between zeroth order diffraction signals upon illumination thereof. For example, additional target layer(s) 145 may be above or below initial layer 90 (illustrated in FIGS. 2A and 2B, respectively). Unresolved pitch $P_2$ may e.g., be half the resolved pitch $P_1$. Unresolved pitch $P_2$ and the position and distance of layer 145 with respect to layer 90 may be selected to yield specified first phase shift 121, which may be 180°, but may as well have another value which is complemented by second phase shift 122 of optical system 150 to yield the 180° overall phase shift to cancel out the zeroth diffraction orders. In the illustrated way, the unresolved periodic structures in any intermediate or underlayer may be used for target design optimization for side-by-side and grating-over-grating targets.

Unresolved periodic structures 146 in layer 145 change the effective permittivity of the layer they are placed in, and therefore affect the creation and propagation of diffraction orders within the whole stack. Unresolved dummy structures as well segmentation at pitches close to the design rule pitch may thus enhance sensitivity of the measured targets to polarization. The field fill factor of unresolved dummy structures 145 may also be modified or designed to control the target's response to illumination polarization. In order to avoid possible cross-talk between targets (layers 90) and dummy structures in complimentary layers (layers 145), dummy structure elements 146 may be designed with segmentation in the direction orthogonal to the measured target periodicity direction. Polarizing structure(s) 145 may be segmented along a direction that is perpendicular to a segmentation direction of initial non-polarizing structures 90. Additional layer 145 may therefore be segmented along the Y direction rather than along the illustrated X direction segmentation in FIGS. 2A and 2B.

Target design file of disclosed scatterometry metrology targets 100 are considered part of the present disclosure.

Figure 3:
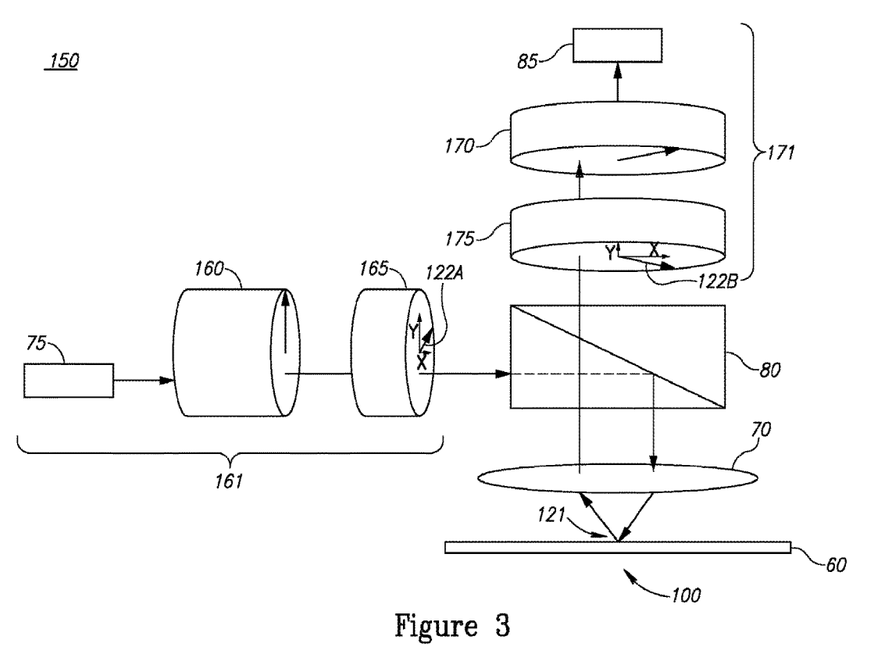
FIG. 3 is a high level schematic illustration of an optical system, according to some embodiments of the invention.

FIG. 3 is a high level schematic illustration of an optical system 150, according to some embodiments of the invention. Optical system 150 comprises an illumination arm 161 with an illumination source 75, a polarizer 160 arranged to polarize the illumination (e.g., linearly) and a first wave plate 165 arranged to determine a phase shift 122A between two orthogonal polarization directions, using the wave-plate parameters (angle and retardation). Optical system 150 further comprises a (non-polarizing or polarizing) beam splitter 80 configured to direct the illumination through an objective 70 on target 100 on a wafer 60 and to direct the diffraction signals from target 100, passing through objective 70, to a collection arm 171. Collection arm 171 comprises a second wave plate 175 at a collection polarization angle 122B, an analyzer 170 and a detector 85. Illumination and collection polarization angles 122A, 122B may be configured to provide second phase shift 122 according to the types of targets and system configuration.

For example, using polarizing targets 100 illustrated in FIGS. 1B and 1C and half-wave plate(s) 165, 175, it suffices that angles 122A, 122B are equal (e.g., 45°) because the full phase shift of 180° is provided by the target as explained above. In another example, using polarizing targets 100 illustrated in FIGS. 2A and 2B, that angles 122A, 122B may be different to provide second phase shift 122 to be added to first phase shift 121 provided by the addition of layer 145 to non-polarizing target 90.

Polarizing beam-splitter 80 may be used instead of or in addition to wave plates 165, 175, and alternatively or complementarily, any optical element may be used to provide a controllable phase shift. For example, using polarizing beam-splitter 80, optical system 150 may be configured to separate optical paths of two perpendicular polarizations and by adding a phase retarder or any other optical element providing an optical path difference between the two polarizations and further combining both polarizations together and using an additional beam-splitter a control on phases of diffraction orders may be achieved.

Optical system 150 may comprise a ND (neutral density) filter in one of optical paths 161, 171, and configured to control the relative amplitudes of the polarizations.

In certain embodiments, only one of wave plates 165, 175 may be used to provide second phase shift 122. In certain embodiments, polarizer 160 and analyzer 170 may be configured to provide and receive, respectively, linearly polarized illumination and diffraction signals, without use of any wave plate 165, 175. For example, polarizer 160 and analyzer 170 may be set at angles of 45° and 135°, correspondingly, for measuring targets such as illustrated in FIGS. 1B, 1C. Optical system 150 may thus be configured to provide a complete zero diffraction order cancellation and a first diffraction order amplitude doubling. FIG. 3 illustrates a very general and robust optical scheme allowing full suppression of zero diffraction order, together with all its lobes due to finite target size, making the system advantageous with respect to using a blocker at the pupil plane as in the prior art. In certain embodiments, the inventors have found that full zero order suppression together with quasi-normal illumination provides the best measurement condition from both the accuracy and the precision points of view.

Polarizer 165 in illumination path 161 and analyzer 170 in collection path 171 may be configured to control a weighting factor of each polarization in the combined signal. Targets 100 may be configured to provide a large sensitivity of the target response to polarization differences, in order to enhance the first order diffraction signal as well as to improve the differentiation between different diffraction orders. Moreover, optical systems 150 and targets 100 may be configured as explained herein to control the amplitude of the zero diffraction order without having a significant effect on the amplitude of the first diffraction orders and/or to control the phase between the zero and the first diffraction orders. The inventors have found out that in the former case imaging contrast enhancement is achieved while in the latter case imaging accuracy enhancement is achieved. In scatterometry (e.g., SCOL—scatterometry overlay), optical systems 150 and targets 100 may be configured to control the phase between the first diffraction orders to enhance both sensitivity and accuracy. In case of scatterometry targets, target designs in different layers may be designed to provide a different response to the change of polarization direction.

Metrology systems, combining optical systems 150 and scatterometry targets 100 of any of the embodiments, are considered part of the present disclosure. In particular, metrology systems are provided, which comprise scatterometry metrology targets 100 having a coarse pitch and configured to yield a first phase shift between zeroth order diffraction signals upon illumination thereof, and metrology tools having optical system 150 configured to illuminate the target by two perpendicularly-polarized illumination components and to analyze a resulting diffraction signal at two perpendicular polarization directions that complement the two perpendicularly-polarized illumination components to yield a second phase shift between zeroth order diffraction signals upon illumination thereof, wherein a sum of the first and second phase shifts is 180° to cancel out the zeroth order diffraction signals.

Figure 4:
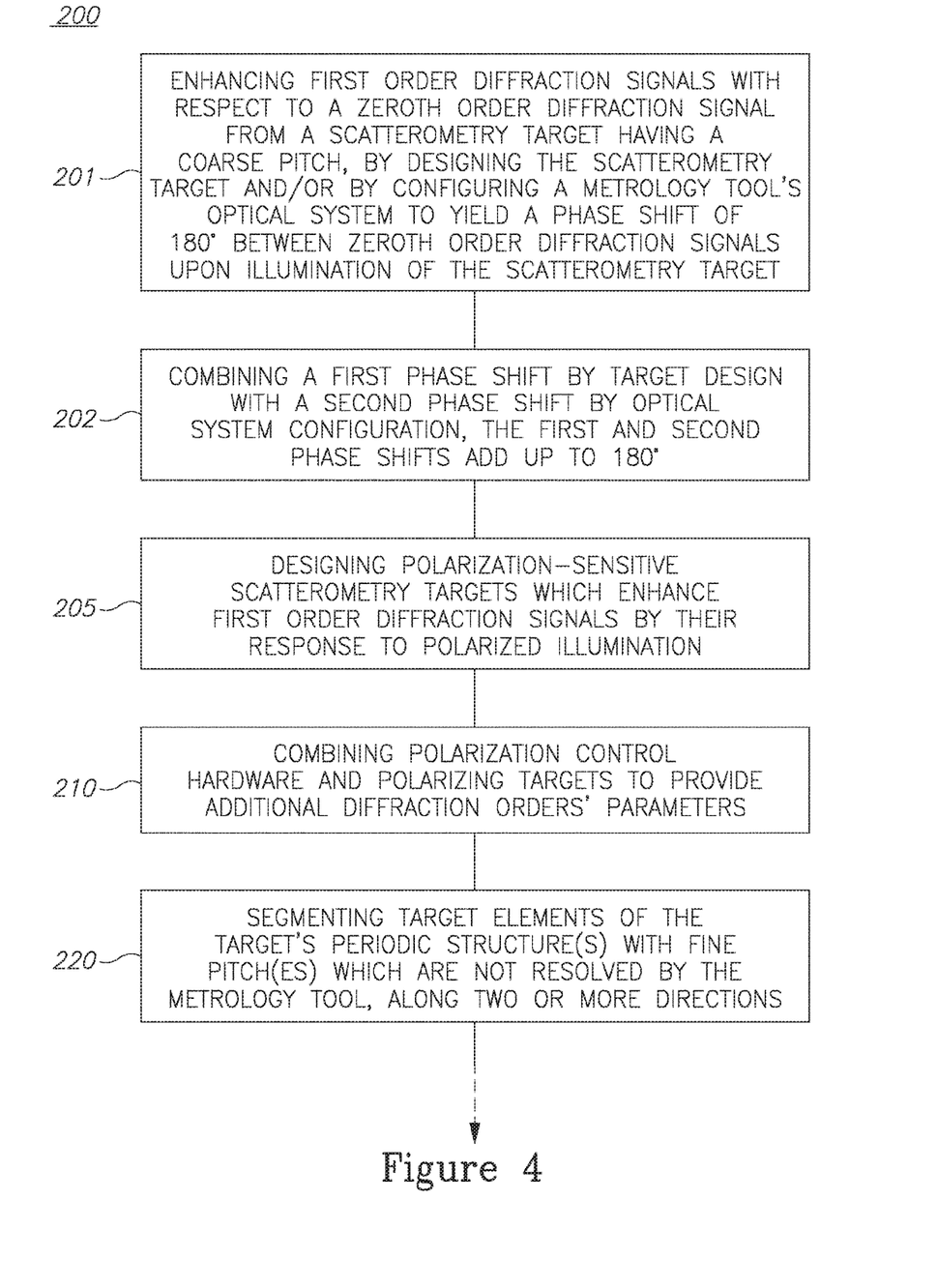
FIG. 4 is a high level flowchart illustrating a method, according to some embodiments of the invention.

FIG. 5 is a high level flowchart illustrating a method 200, according to some embodiments of the invention. Method 200 may be at least partially implemented by at least one computer processor, e.g., in a metrology module. Certain embodiments comprise computer program products comprising a computer readable storage medium having computer readable program embodied therewith and configured to carry out of the relevant stages of method 200. Certain embodiments comprise target design files of respective targets designed by embodiments of method 200.

Method 200 comprises enhancing first order diffraction signals with respect to a zeroth order diffraction signal from a scatterometry target having a coarse pitch, by designing the scatterometry target and/or by configuring a metrology tool's optical system to yield a phase shift of 180° between zeroth order diffraction signals upon illumination of the scatterometry target (stage 201). For example, method 200 may comprise combining a first phase shift by target design with a second phase shift by optical system configuration, the first and second phase shifts add up to 180° (stage 202).

Method 200 may comprise designing scatterometry and/or imaging targets as well as corresponding optical systems for measuring the designed targets. Method 200 may comprise designing polarization-sensitive scatterometry targets which enhance first order diffraction signals by their response to polarized illumination (stage 205) and combining polarizing control hardware and polarizing targets to provide additional diffraction orders parameters (stage 210). Method 200 may further comprise producing the designed target(s) (stage 230) and/or measuring the designed target(s) scatterometrically (stage 235). Method 200 may further comprise configuring the optical system to separate, using illumination polarization, between signals from the orthogonal segmentation regions (stage 240) and controlling the polarization phase in the illumination and/or in the detection optical path (stage 245). Method 200 may comprise configuring the metrology tool's optical system to separate, using illumination polarization, between signals from the orthogonal segmentation regions (stage 242).

Method 200 may comprise segmenting—with at least one fine pitch which is not resolved by a corresponding metrology tool—a plurality of target elements of at least one periodic structure having at least one coarse pitch which is resolved by the corresponding scatterometry metrology tool, wherein the fine segmentation is with respect to at least two directions within at least some of the elements and maintains same zeroth order diffraction parameters in the at least two directions (stage 220). Method 200 may comprise maintaining thereby the same zeroth order diffraction parameters in the different directions (stage 222). Method 200 may designing the scatterometry target to have perpendicularly polarizing elements at half the coarse pitch to yield the 180° phase shift (stage 221).

Method 200 may further comprise additionally segmenting the fine segments perpendicularly by at least one still finer pitch (stage 225).

Method 200 may comprise carrying out measuring 235 using at least two polarized illuminations that correspond to the at least two fine segmentation directions (stage 240), and further comprise interferometrically suppressing zeroth order diffraction signals with respect to the at least two directions and enhancing first order diffraction signals therefrom (stage 250). Method 200 may further comprise interferometrically cancelling out the zeroth order diffraction signals and fully adding the first order diffraction signals, with respect to the at least two directions (stage 255).

Method 200 may further comprise controlling the polarized illuminations and the diffraction signals using corresponding wave plates (stage 260) and possibly allocating and controlling weights of the polarized signals to optimize collected data (stage 265).

Method 200 may comprise configuring the metrology tool's optical system to illuminate the scatterometry target by two perpendicularly-polarized illumination components (stage 270) and analyzing the diffraction signal at two perpendicular polarization directions that complement the two perpendicularly-polarized illumination components to cancel out the zeroth order diffraction signals (stage 275).

Method 200 may comprise designing the scatterometry target, having non-polarizing structures, to have at least one additional target layer having at least one polarizing structure configured to yield the phase shift of 180° (stage 280) and designing the additional target layer(s) to be above and/or below the non-polarizing structures (stage 282).

Advantageously, combining polarizing control hardware (optical system 150) and polarizing targets (targets 100) provide an additional control level of diffraction orders parameters. In targets 100, complementary layers or any available intermediate layer may be used to introduce segmented dummy structures for the purpose of control or enhancement of the polarization properties of the measured targets. Combining polarizing control HW and polarizing targets was found to boost the accuracy and precision in overlay measurements. Optical system 150 and targets 100 may be implemented in various metrology platform and improve the ability to produce device-like targets.

It is emphasized that the design principles disclosed herein enable controlling the phase and/or amplitude of any of the diffraction orders and therefore provide additional advantages beyond zeroth order cancellation.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram portion or portions.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram portion or portions.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram portion or portions.

The aforementioned flowchart and diagrams illustrate the architecture, functionality, and operation of possible implementations of systems, methods and computer program products according to various embodiments of the present invention. In this regard, each portion in the flowchart or portion diagrams may represent a module, segment, or portion of code, which comprises one or more executable instructions for implementing the specified logical function(s). It should also be noted that, in some alternative implementations, the functions noted in the portion may occur out of the order noted in the figures. For example, two portions shown in succession may, in fact, be executed substantially concurrently, or the portions may sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method comprising:
enhancing first order diffraction signals with respect to a zeroth order diffraction signal from a scatterometry target having a coarse pitch, by designing the scatterometry target and/or by configuring a metrology tool's optical system to yield a phase shift of 180° between zeroth order diffraction signals upon illumination of the scatterometry target; and
configuring the metrology tool's optical system to illuminate the scatterometry target by two perpendicularly-polarized illumination components and analyzing the diffraction signal at two perpendicular polarization directions that complement the two perpendicularly-polarized illumination components to cancel out the zeroth order diffraction signals.

2. The method of claim 1, further comprising designing the scatterometry target to have polarizers at half the coarse pitch to yield the 180° phase shift, wherein the polarizers are configured to be perpendicularly polarizing.

3. The method of claim 1, further comprising combining a first phase shift by target design with a second phase shift by optical system configuration, wherein a sum of the first and second phase shifts is 180°.

4. The method of claim 1, further comprising designing the scatterometry target, having non-polarizing structures, to have at least one additional target layer having at least one polarizing structure configured to yield the phase shift of 180°.

5. The method of claim 4, wherein the at least one additional target layer is above the non-polarizing structures.

6. The method of claim 4, wherein the at least one additional target layer is below the non-polarizing structures.

7. A scatterometry metrology target having a coarse pitch and configured to yield a phase shift of 180° between zeroth order diffraction signals upon illumination thereof, wherein a first part of an area with the coarse pitch is segmented in one direction and a second part of the area with the coarse pitch is segmented in a perpendicular direction to that of the first area, and wherein the target has initial non-polarizing structures, and at least one additional target layer having at least one polarizing structure configured to yield the phase shift of 180°.

8. The scatterometry metrology target of claim 7, designed to have polarizers at half the coarse pitch to yield the 180° phase shift, wherein the polarizers are configured to be perpendicularly polarizing.

9. The scatterometry metrology target of claim 8, wherein the polarizers are segmented at a fine pitch.

10. The scatterometry metrology target of claim 7, wherein the at least one polarizing structure is segmented at a fine unresolved pitch.

11. The scatterometry metrology target of claim 10, wherein the at least one polarizing structure is segmented along a direction that is perpendicular to a segmentation direction of the initial non-polarizing structures.

12. The scatterometry metrology target of claim 7, wherein the additional target layer is above the non-polarizing structures.

13. The scatterometry metrology target of claim 7, wherein the additional target layer is below the non-polarizing structures.

14. A metrology tool having an optical system configured to illuminate a non-polarizing scatterometry target by two perpendicularly-polarized illumination components and to analyze a resulting diffraction signal at two perpendicular polarization directions that complement the two perpendicularly-polarized illumination components to cancel out the zeroth order diffraction signals by configuring the illumination and the analysis to yield a phase shift of 180° between identical zeroth order diffraction signals from the scatterometry target.

15. The metrology tool of claim 14, wherein the optical system comprises, for controlling a polarization of the illumination and the diffraction signals, at least one of: a polarizer and an analyzer, at least one wave plate, at least one polarizing beam splitter and at least one neutral density filter.

16. A metrology system, comprising:
a scatterometry metrology target having a coarse pitch and configured to yield a first phase shift between zeroth order diffraction signals upon illumination thereof, and
a metrology tool having an optical system configured to illuminate the target by two perpendicularly-polarized illumination components and to analyze a resulting diffraction signal at two perpendicular polarization directions that complement the two perpendicularly-polarized illumination components to yield a second phase shift between zeroth order diffraction signals upon illumination thereof,
wherein a sum of the first and second phase shifts is 180° to cancel out the zeroth order diffraction signals.

17. The metrology system of claim 16, wherein the optical system comprises, for controlling a polarization of the illumination and the diffraction signals, at least one of: a polarizer and an analyzer, at least one wave plate, at least one polarizing beam splitter and at least one neutral density filter.

18. The metrology system of claim 16, wherein the first phase shift is 180° and the second phase shift is zero.

19. The metrology system of claim 18, wherein the scatterometry metrology target is configured to yield a phase shift of 180° between zeroth order diffraction signals upon illumination thereof.

20. The metrology system of claim 19, designed to have polarizers at half a coarse pitch of the target to yield the 180° phase shift, wherein the polarizers are configured to be perpendicularly polarizing.

21. The metrology system of claim 16, wherein the target has initial non-polarizing structures, and at least one additional target layer having at least one polarizing structure configured to yield the first phase shift.

22. A scatterometry metrology target having a coarse pitch and configured to yield a phase shift of 180° between zeroth order diffraction signals upon illumination thereof, wherein a first part of an area with the coarse pitch is segmented in one direction and a second part of the area with the coarse pitch is segmented in a perpendicular direction to that of the first area, wherein the scatterometry metrology target is designed to have polarizers at half the coarse pitch to yield the 180° phase shift, and wherein the polarizers are configured to be perpendicularly polarizing.

23. The scatterometry metrology target of claim 22, wherein the polarizers are segmented at a fine pitch.

* * * * *